(12) United States Patent
Young (10) Patent No.: US 11,819,824 B2
(45) Date of Patent: *Nov. 21, 2023

(54) SURFACE COATINGS FOR SELF-DECONTAMINATION (71) Applicant: Pure-Light Technologies, Inc., Rigby, ID (US)

(72) Inventor: Roger K. Young, Menan, ID (US)

(73) Assignee: Pure-Light Technologies, Inc., Rigby, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/393,065

(22) Filed: Aug. 3, 2021

(65) Prior Publication Data

US 2022/0040674 A1 Feb. 10, 2022

Related U.S. Application Data (60) Provisional application No. 63/062,582, filed on Aug. 7, 2020.

(51) Int. Cl.
*B01J 21/00* (2006.01)
*B01J 21/06* (2006.01)
(Continued)

(52) U.S. Cl.
CPC ............ *B01J 21/063* (2013.01); *A61L 2/232* (2013.01); *B01J 23/06* (2013.01); *B01J 23/14* (2013.01);
(Continued)

(58) Field of Classification Search
None
See application file for complete search history.

(56) References Cited

U.S. PATENT DOCUMENTS

2009/0008667 A1* 1/2009 Fujii ................ H01L 51/0005
438/22
2009/0269510 A1* 10/2009 Lieberman ............ C23C 18/143
118/620
(Continued)

FOREIGN PATENT DOCUMENTS

CA 2594857 A1 8/2006
CN 104741069 A * 7/2015
(Continued)

OTHER PUBLICATIONS

WO-2011118073-A1—English translation (Year: 2011).*
(Continued)

*Primary Examiner* — Stefanie J Cohen (57) ABSTRACT

An apparatus includes a substrate having a surface and a transparent photocatalyst coating secured on the surface of the substrate, wherein the transparent photocatalyst coating includes titanium oxide and a component selected from a fluorescent dye, ultra-fine glitter, indium tin oxide, aluminum zinc oxide, silver nitrate, and combinations thereof. The substrate is preferably selected from an appliance handle, doorknob, switch, keyboard, countertop, appliance handle, equipment button, touchscreen, handrail, light emitting device, and light cover. Such substrates are frequently touched by one or more users and may become contaminated. However, the transparent photocatalyst coating may be self-decontaminating.

20 Claims, 2 Drawing Sheets (51) Int. Cl.
  B01J 35/00   (2006.01)
  B01J 23/14   (2006.01)
  B01J 27/25   (2006.01)
  A61L 2/232   (2006.01)
  B01J 23/06   (2006.01)
  A61L 101/30  (2006.01)

(52) U.S. Cl.
  CPC ............. B01J 27/25 (2013.01); B01J 35/004 (2013.01); *A61L 2101/30* (2020.08)

(56)         References Cited

U.S. PATENT DOCUMENTS

| | | | | |
|---|---|---|---|---|
| 2010/0158851 | A1* | 6/2010 | Yeung ................ | A01N 59/16 424/641 |
| 2010/0304120 | A1* | 12/2010 | Tokudome ............ | C09D 5/028 524/588 |
| 2011/0118384 | A1* | 5/2011 | Bugnon ............... | C09D 5/032 523/171 |
| 2012/0305061 | A1* | 12/2012 | O'Brien ............... | C03C 17/006 977/773 |
| 2013/0102953 | A1* | 4/2013 | Subrahmanyam ..... | B01J 21/063 502/7 |
| 2014/0336039 | A1* | 11/2014 | Cohen ................. | C09D 5/006 502/159 |
| 2015/0102258 | A1* | 4/2015 | Humle ................ | B01J 37/0018 502/158 |

FOREIGN PATENT DOCUMENTS

| | | | | |
|---|---|---|---|---|
| CN | 104741069 | A | | 7/2015 |
| CN | 106019789 | A | | 10/2016 |
| CN | 106029798 | A | * | 10/2016 ............ C08J 7/0427 |
| CN | 110645074 | A | | 1/2020 |
| JP | 2005131604 | A | | 5/2005 |
| JP | 2007144403 | A | | 6/2007 |
| JP | 2009012444 | A | | 1/2009 |
| WO | WO2007052587 | A1 | | 10/2007 |
| WO | WO-2011118073 | A1 | * | 9/2011 ............ B01J 35/004 |
| WO | WO2011118073 | A1 | | 9/2011 |

OTHER PUBLICATIONS

CN-104741069-A—English translation (Year: 2015).*
CN-106029798-A—English translation (Year: 2016).*
Breval, Elmito, "USPTO Office Action dated Nov. 8, 2022", pp. 1-9.
Breval, Elmito, USPTO Final Office Action dated Mar. 23, 2023, pp. 1-11.
Cohen, Stefanie J., "USPTO Office Action dated Aug. 2, 2022", pp. 1-31.
Cohen, Stefanie J., "USPTO Office Action dated Feb. 7, 2023", pp. 1-10.
Stanek, Kelsey L., "USPTO Office Action dated Sep. 23, 2022", pp. 1-15.
Stanek, Kelsey L., "USPTO Notice of Allowance and Fee(s) Due" dated Mar. 22, 2023; 5 pages.
Streets, Jeffrey L., "Response (Amendment) to Office Action dated Nov. 8, 2022", filed on Jan. 17, 2023; 25 pages.
Streets, Jeffrey L., "Response (Amendment) to Office Action dated Aug. 2, 2022", filed on Nov. 29, 2022; 19 pages.
Streets, Jeffrey L., "Response (Amendment) to Office Action dated Sep. 22, 2022", filed on Dec. 22, 2022; 8 pages.

* cited by examiner

SURFACE COATINGS FOR SELF-DECONTAMINATION

CROSS-REFERENCE TO RELATED APPLICATIONS

This application is a nonprovisional patent application claiming the benefit of U.S. provisional patent application Ser. No. 63/062,582 filed on Aug. 7, 2020, which application is incorporated by reference herein in its entirety.

BACKGROUND

The present disclosure relates to surface coatings applied to surfaces that are exposed to contamination, such as residential and commercial surfaces and furnishings.

BACKGROUND OF THE RELATED ART

Residential and commercial surfaces and furnishings may become contaminated over time due to exposure to environmental contaminants and human or animal contact. For example, any number of people may touch or otherwise contact residential flooring, walls, countertops, and doorknobs, spreading oil and germs on the contacted surfaces. These surfaces may require regular cleaning with chemicals and/or mechanical means. However, it is not uncommon for these surfaces to be in use for long periods of time with being cleaned to any great extent. Bacteria, viruses, and other contaminants may exist on these surfaces for days or weeks and may be spread to other people that come into contact with those surfaces between cleanings. Furthermore, merely wiping down a surface with water may make the surface appear clean but may do very little to reduce contamination of the surface.

BRIEF SUMMARY

Some embodiments provide an apparatus comprising a substrate having a surface, and a transparent semiconductor photocatalyst layer secured to the surface of the substrate, wherein the transparent semiconductor photocatalyst layer includes titanium oxide and a component selected from a fluorescent dye, ultra-fine glitter, indium tin oxide, aluminum zinc oxide, and/or silver nitrate.

Some embodiments provide a formulation for forming a photocatalyst coating on a substrate, comprising an aqueous mixture of titanium oxide and amorphous titanium peroxide, wherein the aqueous mixture further includes a fluorescent dye, ultra-fine glitter, indium tin oxide, aluminum zinc oxide, and/or silver nitrate.

Some embodiments provide an apparatus comprising a substrate having a surface, a transparent binder layer secured to the surface of the substrate, and a transparent semiconductor photocatalyst layer secured to the transparent binder layer, wherein the transparent binder layer and/or the transparent semiconductor photocatalyst layer includes titanium oxide and a component selected from a fluorescent dye, ultra-fine glitter, indium tin oxide, aluminum zinc oxide, and/or silver nitrate.

Some embodiments provide an apparatus, comprising a substrate having a surface, and a photocatalyst coating secured on exposed surface of the substrate, wherein the photocatalyst coating includes titanium oxide and a component selected from a fluorescent dye, ultra-fine glitter, indium tin oxide, aluminum zinc oxide, and/or silver nitrate. The substrate may be any item that comes into contact with contaminants, such as residential or commercial surfaces or furnishings, household goods, business equipment, public structures and the like. Non-limiting examples of the apparatus may include a substrate selected from a floor tile, countertop, appliance handle, equipment button, touchscreen, doorknob, handrail, light emitting device, light cover, switch, and keyboard. Optionally, the exposed surface of the substrate may be a decorative surface, and wherein the photocatalyst coating is transparent.

DETAILED DESCRIPTION

The various embodiments provide photocatalytic formulations, photocatalytic coatings that are prepared using the photocatalytic formulations, substrates and devices that are coated with the photocatalytic coating, methods for preparing the formulation, and methods for forming the coating on a substrate or device.

In some embodiments, the formulation is a solution (a yellow suspension) including anatase titanium oxide having a pH in a range from about 7.5 to about 9.5 and a particle size in a range from about 8 to about 20 nanometers (nm). The formulation may be prepared by adding an alkali hydroxide, such as aqueous ammonium hydroxide or sodium hydroxide to an aqueous titanium salt solution, then washing and separating the resulting titanium hydroxide. The resulting light bluish-white titanium hydroxide may then be treated with an aqueous hydrogen peroxide solution to obtain a yellow, transparent solution of amorphous titanium peroxide sol having a pH in a range from about 6.0 to about 7.0 and a particle size in a range from about 8 to about 20 nm. The amorphous titanium peroxide solution may be heated to a temperature of 100 degrees Celsius or higher, which has been found to reduce the band gap of the resulting photocatalytic coating.

When a semiconductor, such as titanium dioxide, in the coating is irradiated with light (photons) whose wavelength has an energy greater than a band gap of the semiconductor, an electron is promoted to the conduction band such that the electron may participate in an oxidation-reduction reaction with molecules that are in contact with the semiconductor surface. Such a semiconductor is referred to as a "photocatalytic semiconductor" or merely a photocatalyst. Photocatalysts may be in the form of a powder and may be used as suspended in a solution or may be used as supported on a substrate. From the standpoint of photocatalytic activity, the photocatalyst may have greater activity suspended in a solution owing to the greater surface area. However, practical applications of the photocatalyst typically require the photocatalyst to be supported on a substrate.

It is believed that a photon of light having sufficient energy causes separation of an electron (negatively charged) and a hole (positively charged) in the solid phase photocatalyst(s) of the coating. While an electron may cause a reductive reaction with molecules that are in contact with the coating adjacent the electron, the hole may cause an oxidative reaction with molecules that are in contact with the coating adjacent the hole. Accordingly, the photocatalyst may support both oxidative reactions (i.e., oxidation) and reductive reactions (i.e., reduction) at various points over the surface of the photocatalyst coating. These reactions may, without limitation, include the oxidation of water molecules (i.e., moisture in the air or liquid water) and/or the reduction of oxygen molecules (i.e., oxygen in the air or oxygen diffused in liquid water). For example, the oxidation reaction may produce a hydroxyl radical ($^-OH$) and the reduction reaction may produce a super oxygen radical ($O_2^-$). These hydroxyl radicals and super oxygen radicals are very oxidative and non-selective, such that these radicals will react with and destroy organic contaminants with only harmless and naturally occurring byproducts (i.e., water ($H_2O$) and carbon dioxide ($CO_2$)). Accordingly, the hydroxyl radicals produced by the photocatalysts are effective at eliminating volatile organic compounds (VOCs), viruses, bacteria, pollen, mold, and other pollutants and contaminants.

In some embodiments, the formulation may further include a fluorescent dye that is incorporated into the coating. After applying the formulation to a surface and allowing it to dry and harden, the resulting coating is transparent. This prevents any simple determination whether the coating has achieved full coverage over a particular substrate or whether the coating remains adhered to the substrate over time. However, with a fluorescent dye added to the formulation that is used to form the coating, ultraviolet light that is directed at the photocatalytic coating will cause the fluorescent dye in the coating to emit a fluorescence that can be easily seen. The observation of fluorescence makes it easy to determine that the coating covers the intended area of the substrate and/or is still attached to the substrate. The amount of fluorescent dye that is added to the formulation may vary from one application to the next. However, the fluorescent dye may be less than 1 percent of the formulation and is preferably about 0.5 percent of the formulation, such as from 0.4 to 0.6 percent of the formulation. A non-limiting example of a fluorescent dye is triethanolamine ($N(CH_2CH_2OH)_3$). A suitable concentration is between about 2 and about 10 mg/m² of the coated surface, and most preferably about 5 mg/m² of the coated surface.

Similarly, in some embodiments, the formulation may include ultra-fine glitter added to the formulation to assist in ascertaining whether the coating has achieved full coverage over an intended area of a substrate and/or whether the coating remains adhered to the substrate over time.

In some embodiments, the formulation may further include an additional photocatalytic oxide for the purpose of enhancing the photocatalytic action of the coating. For example, the further photocatalytic oxide may be selected from indium tin oxide (ITO) and/or aluminum zinc oxide ($Al_2O_5Zn_2$). Including one or both of these photocatalytic oxides in the formulation may reduce the band gap of the coating formed with the formulation. Reducing the band gap means that the coating will have a greater level of photocatalytic action in response to a given amount of light exposure. So, if the coating includes titanium dioxide and one or more of indium tin oxide (ITO) and/or aluminum zinc oxide ($Al_2O_5Zn_2$), then the band gap of the coating may be reduced below the band gap for titanium dioxide alone.

The band gap energy of a semiconductor is the minimum energy required to excite an electron in the valence band and promote that electron into the conduction band where it can participate in conduction. In graphs of the electronic band structure of insulators and semiconductors, the band gap generally refers to the energy difference between the top of the valence band and the bottom of the conduction band. The addition of indium tin oxide may, for example, decrease the indirect band gap of titanium dioxide present in the coating. It is believed that the indium tin oxide may increase electron mobility of the semiconductor. Accordingly, less energy is required to move an electron from the valence band to the conduction band. When the titanium dioxide is subjected to photons, the photons pass their energy to electrons in the titanium dioxide material. This energy provides those electrons with enough energy to move from the valence band to the conduction band. The amount of energy required to make this happen is called a band gap or energy gap.

Anatase titanium dioxide is an indirect band gap semiconductor that possesses a band gap value ranging from about 3.2 to about 3.35 electronvolts (eV) in the thin film state. As a non-limiting example, the thin film may have a thickness between about 75 and about 300 microns. The band gap of a thin film of anatase titanium dioxide can be reduced to about 2 eV with heating. Formulations including a further photocatalytic oxide, such as indium tin oxide (ITO) and/or aluminum zinc oxide ($Al_2O_5Zn_2$), are believed to reduce the band gap to about 1 eV.

In some embodiments, silver nitrate ($AgNO_3$) may be added to the formulation to provide the resulting coating with antimicrobial activity even in the absence of light. Coatings that contain silver nitrate may be beneficially applied to surfaces that a person is likely to contact. For example, countertops, doorknobs, mobile phones, touch screens and control panels are frequently touched by one or more people. A surface that supports the coating with silver nitrate may immediately begin decontaminating any organic matter that is left on the surface by a person's touch even in the dark.

In some embodiments, an ultra-fine glitter may be added to the formulation.

In one embodiment, a photocatalyst coating may be formed on the surface of a substrate and may then be either air dried or heat dried. Heat drying is preferred as it has been found to decrease the band gap. The photocatalyst coating may be formed as a single layer coating containing the photocatalyst or may be formed as a two-layer coating including a binder layer followed by a photocatalyst layer.

Some embodiments provide a method for forming a photocatalytic coating on a substrate. The photocatalyst coating may be secured directly to a surface of the substrate or secured to an optional binder layer that secured to the substrate. For example, an amorphous titanium peroxide sol may be used as a binder to secure the photocatalyst to the substrate. A "sol" is a colloid made of very small solid particles in a continuous liquid medium.

In some embodiments, the substrate may be the lightbulb cover, such as a bulb made of glass, fused quartz or plastic. The light within the cover or bulb may be produced by an incandescent element (i.e., wire filament), a fluorescent element (i.e., cathode electrodes and a gas, such as mercury vapor), or a light-emitting diode.

In some embodiments, a method for forming or securing a photocatalyst to a substrate includes applying multiple layers of an amorphous titanium peroxide sol to the substrate or an optional binder layer. For example, a first layer of an amorphous titanium peroxide sol may be applied onto the substrate or binder layer, and then a second layer may be applied onto the first layer, wherein the second layer is made of a mixture of the photocatalyst and an amorphous titanium peroxide sol. Optionally, the amorphous titanium peroxide sol may have no photocatalytic function.

Some embodiments provide a photocatalytic body or apparatus prepared in accordance with one or more of the methods. For example, the photocatalytic body may include a substrate and a photocatalytic coating secured to a surface of the substrate. Optionally, the photocatalytic body may include a binder layer between the surface of the substrate and a photocatalyst layer.

Some embodiments provide a photocatalyst formulation used in the method for forming the photocatalytic coating on a substrate. The photocatalyst formulation may be applied directly onto a substrate or onto a layer of a binder material. Optionally, the binder may be formed from an amorphous titanium peroxide sol.

In some embodiments, an amorphous titanium peroxide sol may be prepared from an aqueous solution of a titanium salt, such as titanium tetrachloride ($TiCl_4$), by adding an alkali hydroxide, such as aqueous ammonium hydroxide or sodium hydroxide. The reaction product formed by the addition of alkali hydroxide to the aqueous solution of a titanium salt is a light bluish-white, amorphous titanium hydroxide ($Ti(OH)_4$) that may be referred to as ortho-titanic acid ($H_4TiO_4$). This titanium hydroxide may be washed and separated, then treated with an aqueous hydrogen peroxide solution to obtain an amorphous titanium peroxide solution that may be used to form the binder layer and/or used in the photocatalyst layer. The amorphous titanium peroxide sol may have a pH in a range from about 6.0 to about 7.0, may have a particle size in a range from about 8 nanometers to about 20 nanometers (nm), and may appear as a yellow transparent liquid. The amorphous titanium peroxide sol is stable when stored at temperatures between about 45 and about 65 degrees Celsius over an extended period of about 6 months. The sol concentration may be adjusted to a range from about 1.40% to about 1.60% amorphous titanium peroxide by volume. For example, the concentration of the amorphous titanium peroxide sol may be reduced by dilution with a liquid, such as distilled water.

The amorphous titanium peroxide sol may remain in the amorphous form, since amorphous titanium peroxide is not crystallized into the form of anatase titanium oxide at normal temperatures, such as temperatures between about 45 and about 65 degrees Celsius. The amorphous titanium peroxide sol has good adherence to a substrate surface, a good film-forming property and is able to form a uniform thin film on almost any substrate. Once the amorphous titanium peroxide sol film has been dried, the dried film or coating is insoluble in water. Conversely, if the amorphous titanium peroxide sol is heated to 100 degrees Celsius (° C.) or greater, the amorphous titanium peroxide sol is converted to an anatase titanium oxide sol. Similarly, an amorphous titanium peroxide sol that has been applied to a substrate, and has been dried and fixed on the substrate, may be converted to anatase titanium oxide when heated to 250 degrees C. or greater.

Some embodiments may use one or more photocatalysts in the photocatalyst layer. Each of the one or more photocatalysts may be independently selected from $TiO_2$, ZnO, $SrTiO_3$, CdS, CdO, CaP, InP, $In_2O_3$, CaAs, $BaTiO_3$, $K_2NbO_3$, $Fe_2O_3$, $Ta_2O_5$, $WO_3$, $SaO_2$, $Bi_2O_3$, NiO, $Cu_2O$, SiC, $SiO_2$, $MoS_2$, $MoS_3$, InPb, $RuO_2$, $CeO_2$ and the like. A preferred photocatalyst is titanium dioxide ($TiO_2$). A formulation containing titanium dioxide, also referred to as titanium oxide, may be used in the form of a sol.

In some embodiments, a titanium oxide sol may be prepared by heating an amorphous titanium peroxide sol at a temperature of 100° C. or greater, where the amorphous titanium peroxide sol may be prepared as described above. The properties of the titanium oxide sol may vary slightly depending upon the temperature at which the amorphous titanium peroxide sol is heated and the duration of time over which the heating takes place. For instance, an anatase titanium oxide sol that is formed by heating an amorphous titanium peroxide sol at 100° C. for 6 hours may have a pH ranging from about 7.5 to about 9.5, may have a particle size ranging from about 8 nanometers to about 20 nanometers, and may appear as a yellow suspension.

The titanium oxide sol is stable when stored at normal temperatures over a long time and may form a precipitate on mixing with an acid or a metal aqueous solution. Moreover, the sol may be impeded in its photocatalytic activity or an acid resistance when Na ions co-exists. The titanium oxide sol concentration may be adjusted to within a range from about 1% to about 5% by volume, and preferably about 2.70% to about 2.90% by volume prior to use.

In some embodiments, the substrate may be made of various inorganic materials, such as ceramics and glass. In other embodiments, the substrate may be made of various organic materials, such as plastics, rubber, wood, and paper. In still other embodiments, the substrate may be made of various metals, such as aluminum, steel and various alloys. In particular, the amorphous titanium peroxide sol may bind well with certain organic polymer resin materials, such as acrylonitrile resin, vinyl chloride resin, polycarbonate resins, methyl methacrylate resin (acrylic resins), polyester resins, and polyurethane resins. The substrate may also be provided in various sizes and shapes, such as a honeycomb, fibers, a filter sheet, a bead, a foamed body, a smooth flat or curved surface, or combinations thereof. Substrates that transmit UV light therethrough may have the photocatalytic coating applied to an inner or outer surface of the substrate. Still further, the photocatalytic coatings may be applied to substrates that have already been coated with other materials.

In some embodiments, the binder layer is formed with materials that will not be decomposed by the action of the photocatalyst layer. For example, an inorganic binder may be inert to the free radical species generated by the photocatalytic reactions occurring at the photocatalyst surface. Non-limiting examples of inorganic binders include water glass, colloidal silica, and cement. A preferred inorganic binder may be formed from an amorphous titanium peroxide sol. Non-limiting examples of organic binders that may be inert include fluoropolymers and silicone polymers.

In some embodiments, a formulation that is used to make the photocatalytic layer may be a mixed sol including a uniform suspension of titanium oxide powder in an amorphous titanium peroxide sol. For example, the titanium oxide powder may be uniformly suspended in the amorphous titanium peroxide sol by mechanical mixing followed by the application of ultrasonic waves.

Next, the titanium oxide sol and the amorphous titanium oxide sol may be mixed to obtain a mixed sol. The mixing ratio may vary depending upon the end use of the photocatalyst coating. For example, the mixing ratio may vary depending on the portion of a product to which the photocatalytic layer is applied and the conditions under which the photocatalyst layer will be used. Furthermore, the mixing ratio may be determined with consideration given to the necessary adherence of the coating to a substrate, the film-forming properties of the mixture, the corrosion resistance of the mixture, and the decorativeness of the photocatalytic layer made by use of the mixed sol. The mixing ratio may be based upon the types of articles to which the coating is to be applied. Three group of substrates may be broadly classified as follows:

(1) Those articles which a person may contact or touch, or is highly likely to contact or touch, and which need decorativeness from a visual standpoint, e.g. interior tiles, sanitary wares, various types of unit articles, table wares, exterior materials in buildings, interior automotive trims and the like.

(2) Those articles which a person does not contact or touch, but requires visual decorativeness, e.g. exterior panels for light fittings, underground passage, tunnel, materials for engineering works, and electrical equipment.

(3) Those articles which a person does not usually contact, touch, or see and in which the function of decomposing organic matters based on a photocatalytic function or the properties inherent to semiconductive metals are utilized, e.g. built-in members in the inside of water-purifier tanks, various types of sewage treatment equipment, water heaters, bath tubs, air conditioners, the hoods of microwave ovens, and other apparatus.

For an article from group (1), a photocatalytic layer may be prepared with a mixed sol including about 30 weight percent (wt %) or less of the titanium oxide sol based on a total amount of the mixed sol (i.e., the combination of titanium oxide sol and an amorphous titanium peroxide sol). Photocatalyst layers formed with this mixing ratio are suitable for sterilization or decontamination in daily life and also for decomposition of residual odors. Moreover, the coating surface is so hard that it is free of any wear such as by sweeping or dusting and also of any deposition of foreign matters, along with the unlikelihood of leaving fingerprints on contact. In fact, the coating has been found to have a hardness from about 7.0 to about 7.2 on the hardness scale.

An example of an article from group (3) is a water-purifier tank. High photocatalytic activity is the most important property for a photocatalyst in a water-purifier tank, where photocatalytic activity is required to lower a biological oxygen demand (BOD) in final wastewater-treated water. A photocatalytic layer suitable for these applications may be prepared with a mixed sol including about 70 wt % or greater of titanium oxide sol based on the amount of the mixed sol (i.e., the combination of titanium oxide sol and an amorphous titanium peroxide sol). This photocatalytic layer may be poor in decorativeness since a person does not typically contact, touch or see the photocatalytic layer.

For an article from group (2), a photocatalytic layer may be prepared with a mixed sol including from about 20 wt % to about 80 wt % titanium oxide sol based on a total amount of the mixed sol (i.e., the combination of titanium oxide sol and an amorphous titanium peroxide sol). This photocatalytic layer exhibits properties intermediate between the photocatalytic layers described above in reference to groups (1) and (3) with respect to the hardness, the adherence of foreign matters, and the photocatalytic activity.

In some embodiments, a titanium oxide sol, an amorphous titanium peroxide sol and/or a mixed sol may be applied over a surface of a substrate using any known process, including, for example, dipping, spraying, brushing, and coating. The results of coating application are frequently improved by repeating the coating step multiple times.

After applying a layer by any of the processes mentioned above, the sol layer may be dried and solidified to obtain a coating layer, including a binder layer and/or a photocatalyst layer. The sol layer may also be baked at a temperature ranging from about 200° C. to about 400° C.

In some embodiments, the photocatalytic activity of titanium oxide may be reduced by the presence of sodium ions. Accordingly, if the substrate or binder layer is subject to decomposition, such as an organic polymer resin that may undergo decomposition by means of a photocatalyst applied thereto, the substrate or binder layer may be cleaned with a sodium ion-containing material, such as a sodium hydroxide solution, to reduce the extent to which the photocatalyst may decompose the substrate or binder layer.

It will be noted that where an amorphous titanium peroxide sol is used as a first layer, the amorphous titanium peroxide may be converted to the crystals of anatase titanium oxide on heating to 250° C. or greater, thereby causing a photocatalytic function to develop. Accordingly, temperatures lower than 250° C., for example 80° C. or below, may be used for drying and solidification. In this case, sodium ions may be added to the titanium peroxide sol for the reasons set out above.

In some embodiments, a wavelength (absorption band) of UV light that is necessary to induce photocatalytic activity, i.e. an excitation wavelength, may be modified by the altering the composition of the formulation (by addition of inorganic pigments or metals) and/or altering the thermal treatment of the coating. For example, $CrO_3$ may be added to the $TiO_2$ in small amounts so that the absorption band is shifted toward a longer wavelength.

In some embodiments, the photocatalytic layer may be admixed with one or more metals, such as Pt, Ag, Rh, RuO, Nb, Cu, Sn, and NiO, to assist in the photocatalytic activity of the photocatalytic layer. These metals may be added to the formulation at various point in the preparation of the photocatalytic layer.

In some embodiments, a photocatalyst may be supported and fixed on a substrate without lowering the photocatalytic function of the photocatalyst, thereby providing a photocatalytic layer which is usable over a long period of time. The photocatalytic layers and coatings may be used on interior and exterior surfaces and structures of buildings such as interior and exterior tiles, sanitary wares, air conditioners, bathtubs and the like, exterior panels of various types of electric equipment such as lighting fittings, interior automotive members, inner walls of underground passages and tunnels, water-purifier tanks and the like.

Figure 1:
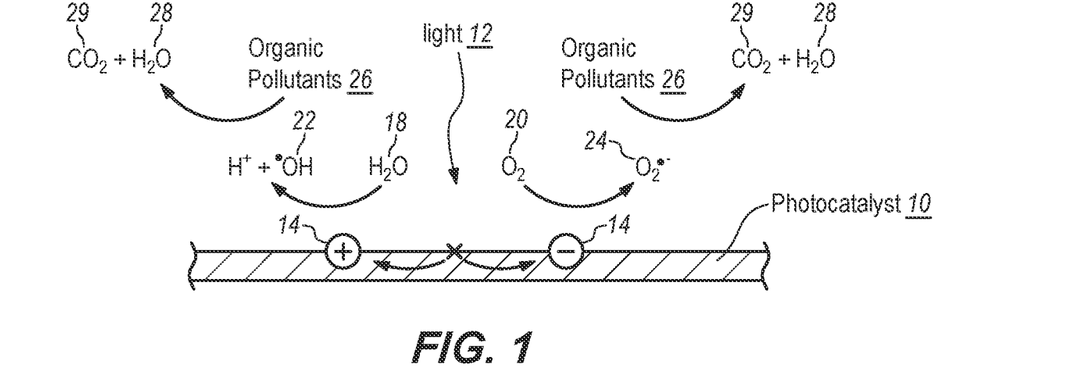
FIG. 1 is a diagram of a photocatalyst absorbing light and producing one or more reactive species capable of degrading an organic pollutant.

FIG. 1 is a diagram of a photocatalyst 10 absorbing light 12 and producing one or more reactive species capable of degrading an organic pollutant. The photocatalyst may take the form of a coating or layer secured to a substrate (not shown) or secured to a binder that is itself secured to a substrate.

It is believed that a photon of light 12 having sufficient energy causes separation of an electron 14 (negatively charged) and a hole 16 (positively charged) in the solid phase photocatalyst(s) 10. While an electron 14 may cause a reductive reaction with molecules that are in contact with the photocatalyst 10 adjacent the electron 14, the hole 16 may cause an oxidative reaction with molecules that are in contact with the photocatalyst 10 adjacent the hole 16. Accordingly, the photocatalyst 10 may support both oxidative reactions (i.e., oxidation) and reductive reactions (i.e., reduction) at various points over the surface of the photocatalyst coating.

These oxidative and reductive reactions may, without limitation, include the oxidation of water molecules 18 (i.e., moisture in the air or liquid water) and/or the reduction of oxygen molecules 20 (i.e., oxygen in the air or oxygen diffused in liquid water). For example, the oxidation of water 18 may produce a hydroxyl radical ($^-$OH) 22 and the reduction of oxygen 20 may produce a super oxygen radical ($O_2^-$) 24. These hydroxyl radicals 22 and super oxygen radicals 24 are very reactive and non-selective, such that these radicals will react with and destroy organic contaminants or pollutants 26 with only harmless and naturally occurring byproducts (i.e., water ($H_2O$) 28 and carbon dioxide ($CO_2$) 29). Accordingly, the reactive species 22, 24 produced by the photocatalyst 10 are effective at eliminating volatile organic compounds (VOCs), viruses, bacteria, pollen, mold, and other organic contaminants or pollutants 26.

Figure 2:
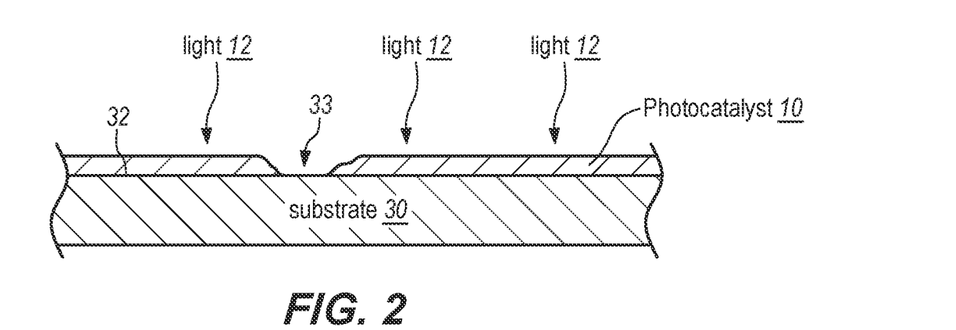
FIG. 2 is a diagram of a substrate and a photocatalytic coating secured to a surface of the substrate.

FIG. 2 is a diagram of a substrate 30 and a photocatalyst coating 10 secured to a surface 32 of the substrate 30. The substrate 30 provides physical support for a thin layer of the photocatalyst 10. Optionally, the photocatalyst could cover all surfaces of a substrate, one side or the other side of substrate, or a limited region of a substrate. A wide variety of substrate materials may be used. Furthermore, the thickness and composition of the photocatalyst may also vary as described herein.

In some embodiments, the photocatalyst 10 may include a fluorescent dye or ultra-fine glitter. The inclusion of fluorescent dye or ultra-fine glitter makes it possible to detect coverage of the photocatalyst over the substrate during or after manufacturing or detect damage that may occur to the photocatalyst coating over time. It is easy for a person making a visual inspection of the photocatalyst 10 having ultra-fine glitter to detect a damaged or uncovered area 33 due to the absence of a glittery appearance. Due to the transparent or translucent nature of the photocatalyst 10, the damaged or uncovered area 33 may otherwise avoid visual detection. In an alternative embodiment, the photocatalyst 10 may include a fluorescent dye, such as triethanolamine ($N(CH_2CH_2OH)_3$). The fluorescent dye shows up when exposed to light of a wavelength known to cause the fluorescence, such as a wavelength from 390 to 420 nanometers. Uncovered or damages areas 33 are visually detectable by the absence of fluorescence in those areas.

Figure 3:
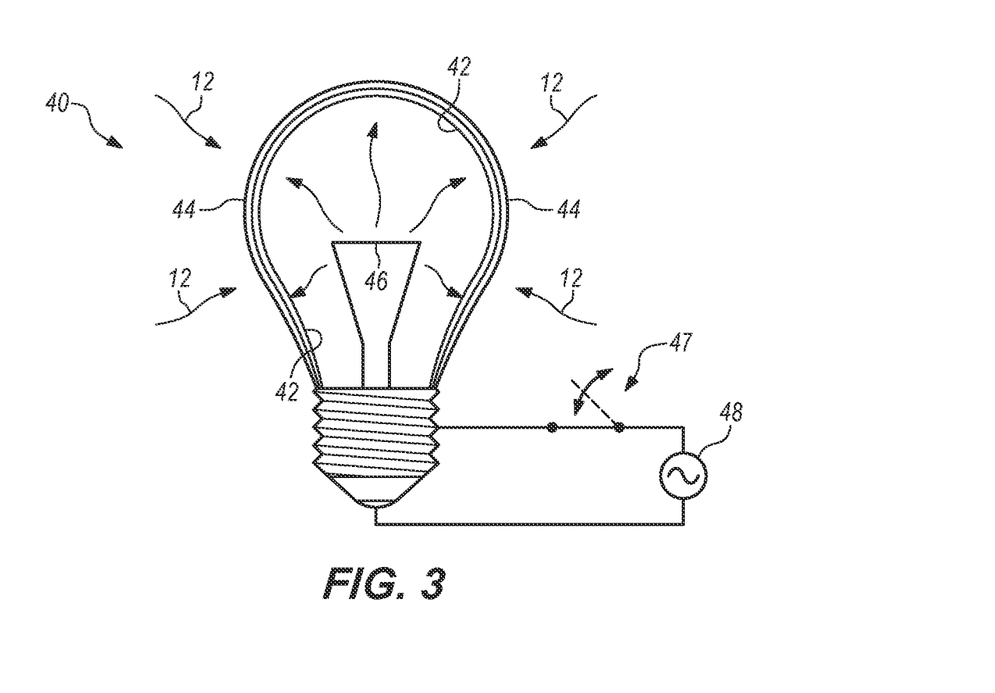
FIG. 3 is a diagram of a transparent substrate in the form of a lightbulb having a photocatalytic coating secured to an exterior surface of the lightbulb.

FIG. 3 is a diagram of a lightbulb 40 including a transparent substrate 42 in the form of a bulb or globe having a photocatalyst coating 44 secured to an exterior surface of the transparent substrate 42. While light 12 from the sun or other sources may activate the photocatalyst 44, the lightbulb 40 includes its own light source, such as a wire filament 46, that emits light (photons), from within the bulb or globe-shaped substrate 42. The substrate may be made of various materials, such as glass, fused quartz or plastic. However, for light from the wire filament 46 to reach the photocatalyst and induce charge separation (i.e., the production of electrons and holes) the substrate may be transparent or translucent. As a result, the photocatalytic activity of the photocatalyst coating 44 is not dependent upon external light sources and can degrade organic pollutants in the air or water surrounding the lightbulb 40 as long as the lightbulb is switched on (see switch 47) to supply electrical current from a source of electrical current 48, such as an alternating current source or battery. Still, the photocatalyst 44 is formed on the external surface of the substrate 42 where it makes contact with oxygen and water in the air surrounding the lightbulb 40. The reactive species formed as a result of light being absorbed by the photocatalyst will then circulate in the air surrounding the lightbulb until the reactive species contact and degrade an organic pollutant.

It should be recognized that the lightbulb 40 of FIG. 3 is representative of other embodiments of a light-emitting device. For example, the wire-filament 46 that is present in most incandescent lightbulbs may be replaced with one or more light-emitting diode (LED) or the components of a fluorescent lightbulb (i.e., fluorescent gas and cathodes). Furthermore, the lightbulb 40 may have a wide variety of shapes as desired for aesthetic or functional purposes. Still further, the photocatalyst 44 may be formed using any of the formulations and methods disclosed herein.

Figures 4, 5A, 5B:
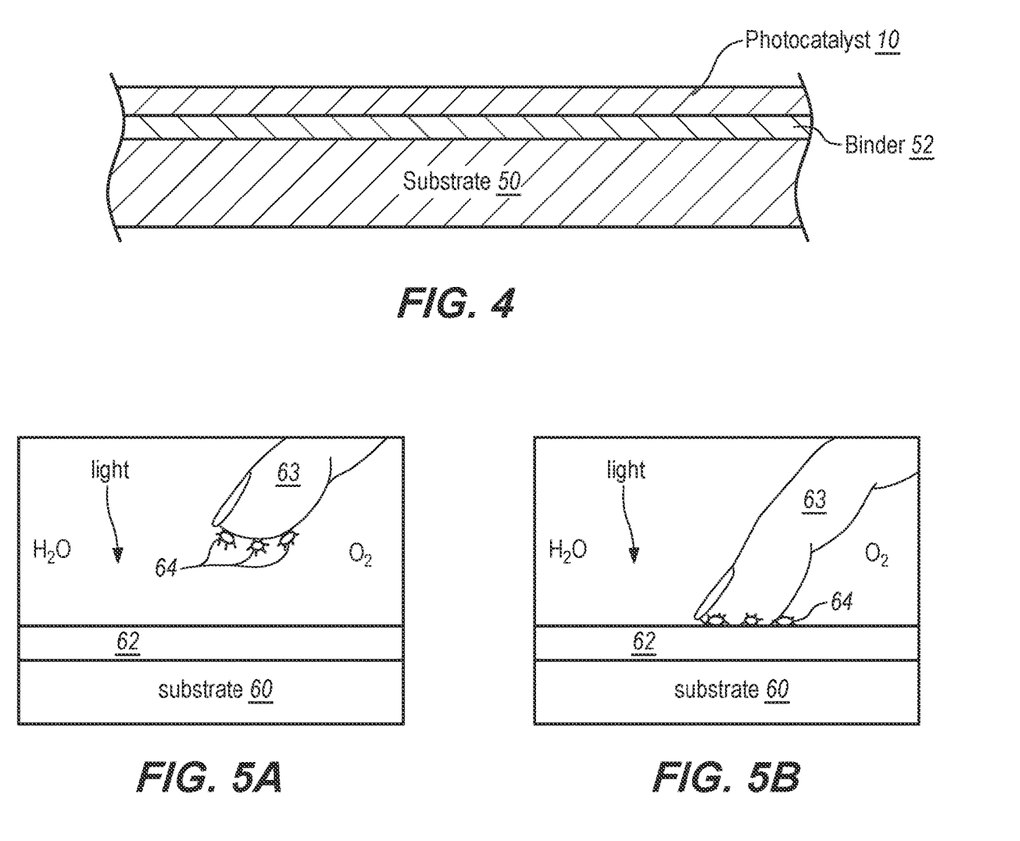
FIG. 4 is a diagram of a substrate, a binder layer secured to the substrate, a photocatalytic coating secured to the binder layer, and a light source directing light on the photocatalytic coating.
FIGS. 5A-D are diagrams of a photocatalyst-coated substrate being contaminated by touching and then being decontaminated by the mechanism of action of the photocatalyst.

FIG. 4 is a diagram of a substrate 50, a binder layer 52 secured to the substrate 50, a photocatalytic coating 10 secured to the binder layer 52. Light may be directed onto the photocatalyst from the top or, if the substrate is transparent or translucent, from the bottom. The binder layer may be used to improve attachment of the photocatalyst to the substrate. However, the binder layer may also include one or more photocatalysts and may contribute additional photocatalytic activity or capacity to the overall structure. The binder layer 52 may also have a different composition than the photocatalyst layer 10 and/or may be processed under different conditions than the photocatalyst layer 10.

FIGS. 5A-D are diagrams of a substrate 60 having a photocatalyst coating 62 that is being contaminated by touching and then being decontaminated by the mechanism of action of the photocatalyst coating 62. The photocatalyst coating 62 is supported by the substrate 60 and is directly exposed to air, moisture and light in the environment. While the light is illustrated reaching the photocatalyst from the exposed (environment) side, it is also possible for a transparent or translucent substrate to allow light to reach the photocatalyst from the substrate side.

In FIG. 5A, a person's finger 63 is contaminated with an organic material 64, such as a virus, bacteria, mold, fungus, oil, dirt or the like. Light absorbed by the photocatalyst 62 may, as described previously (see FIG. 1), form reactive species from the water and oxygen in the air that comes into contact with the photocatalyst 62. Accordingly, the reactive species may circulate in the air to degrade the organic material 64 even in the absence of actual contact between the organic material 64 and the photocatalyst 62.

Figure 5C:
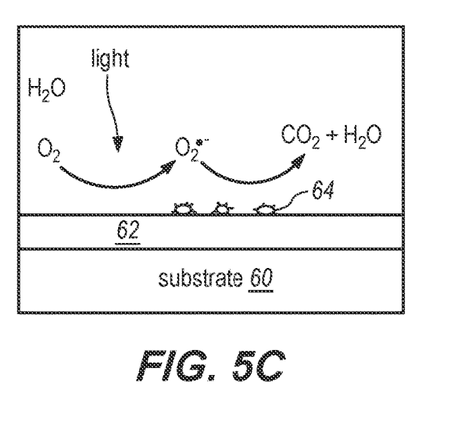
Figure 5D:
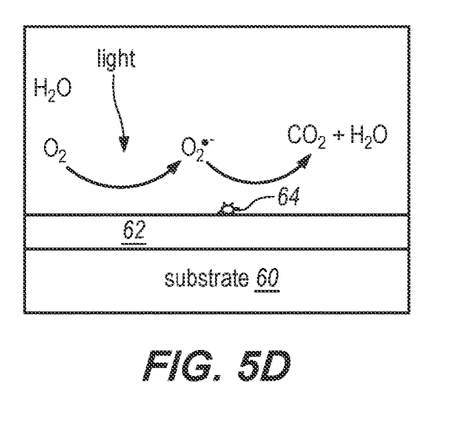

In FIG. 5B, the person's finger 63 contacts the photocatalyst 62. FIG. 5C illustrates the photocatalytic activity of the photocatalyst 62 absorbing light and transforming an oxygen molecule ($O_2$) into a super oxygen radical ($O_2^-$). The super oxygen radical ($O_2^-$) may then degrade some of the organic material 64 to form carbon dioxide and water. With continued exposure to light, the photocatalyst 62 continues to form reactive species, such as the super oxygen radical ($O_2^-$), to degrade additional organic material 64. Because the photocatalyst 62 is not consumed or degraded in the photocatalytic process, the effectiveness of the photocatalyst 62 may continue indefinitely. As shown in FIG. 5D, eventually most or all of the organic material 64 can be eliminated. For many surfaces that are frequently touched by people, such as public door knobs and bathroom faucets, the ability to passively decontaminate the surface at all times is a substantial benefit to health and hygiene.

Some embodiments are more particularly described by way of the following Reference Solutions and Examples, which should not be construed as limiting the scope of the embodiments.

Reference Solution 1 (Preparation of an Amorphous Titanium Peroxide Sol)

A 1:70 dilution by volume of a 50% solution of titanium tetrachloride ($TiCl_4$) with distilled water and a 1:10 dilution by volume of a 25% solution of ammonium hydroxide ($NH_4OH$) with distilled water were mixed at a ratio by volume of 7:1 for a neutralization reaction. After completion of the neutralization reaction, the pH was adjusted to fall into a range from about 6.5 to about 6.8, and the mixture was allowed to stand for about an hour to form a gel, followed by discarding of the supernatant liquid. Distilled water was added to the resultant $Ti(OH)_4$ in an amount of about 4 times the amount of gel, followed by sufficient agitation to mix the water and gel thoroughly, and allowing the mixture to stand. The washing with distilled water was repeated until no chlorine ion was detected in the supernatant liquid. Silver nitrate may be used to detect chlorine. Finally, the supernatant liquid was discarded to leave only a gel. In some cases, the gel may be subjected to centrifugal dehydration to obtain a better gel. 210 ml of an aqueous 35% hydrogen peroxide ($H_2O_2$) solution was divided into two halves and one half was added to 3600 ml of light yellowish white $Ti(OH)_4$ every 30 minutes, followed by agitation at about 5 degrees Celsius overnight to obtain about 2500 ml of a yellow transparent amorphous titanium peroxide sol.

If the temperature of the solutions is not suppressed in the above steps, there is the possibility that water-insoluble matter, such as metatitanic acid deposits, may form. Thus, it is preferred to carry out all the steps while suppressing the temperature of the solutions, such as by directing a fan to blow room temperature or chilled air over the solution.

Reference Solution 2 (Preparation of Titanium Oxide Sol from Amorphous Titanium Peroxide Sol)

Heating the amorphous titanium peroxide sol at 100° C. will cause the amorphous titanium peroxide sol to be converted to anatase titanium oxide after a period of about 3 hours and will cause a further conversion to an anatase titanium oxide sol on heating for about 6 hours. Moreover, when the amorphous titanium peroxide sol is heated at 100° C. for 8 hours, it assumes a light yellow, lightly suspended fluorescence. On concentration of the amorphous titanium peroxide sol, a yellow opaque matter may be obtained. Further, when the amorphous titanium peroxide sol is heated at 100° C. for 16 hours, a very light-yellow matter is obtained. This matter, more or less, lowers in dry adherence on comparison with that obtained by heating at 100° C. for 6 hours. Heating the amorphous titanium peroxide sol (prior to applying over a substrate) for a longer period of time (i.e., about 6 hours) during preparation of the formulation results in a formulation that will form a coating having greater photocatalytic activity but lower adherence to the substrate relative to a coating that is formed with the same starting formulation that was heated for a shorter period of time (i.e., about 3 hours) during preparation of the formulation.

The titanium oxide sol was lower in viscosity than the amorphous titanium oxide and is employed after concentration to 2.5 wt % because of the ease in dipping.

Example 1

The decomposition of organic substances was tested using photocatalytic coatings made from different mixing ratios between the amorphous titanium peroxide sol and the titanium oxide sol. A KERAMIT decorative sheet having dimensions of about 150 mm long, about 220 mm wide, and about 4 mm thick was used as a substrate. Mixed sols having different mixing ratios were each coated onto one of the substrates in a thickness of about 2 micrometers (μm) by spraying and then dried from normal ambient temperatures to 70° C., followed by baking at about 400° C. for 30 minutes to obtain five types of photocatalytic bodies, wherein different types of photocatalysts were each supported on the substrate.

These five photocatalytic bodies were each placed in a test container and a colored solution of an organic substance was added into each test container to a depth of 1 centimeter (cm), covering the photocatalytic body or substrate. The colored solution was a 1:30 dilution of POLLUX Red OM-R (SUMIKA COLOR CO., LTD.) which was an aqueous dispersion (red liquid) of Monoazo Red. In order to prevent the evaporation of the colored solution in the container, the container was covered with a float glass (capable of cutting a wavelength of 300 nm or below). Two UV radiators (each being a 20 W blue color fluorescent tube) were set at 5 cm above the test container and at 9.5 cm from the substrate, while keeping the two UV radiators apart from each other at a distance of 13 cm. The individual photocatalytic bodies were irradiated with UV light and the duration of irradiation was measured. The organic matter was judged to be completely decomposed when the color of the colored solution was bleached.

The photocatalytic body with 100% titanium oxide sol applied onto the substrate was as able to bleach the color in 72 hours from commencement of the test. Thus, the capability of decomposing the organic substance, i.e., the photocatalytic function, was good, but a residue after the decomposition was great in amount.

The photocatalytic body with 100% of the amorphous titanium peroxide sol applied onto the substrate bleached the color in 150 hours from commencement of the test. So, the ability of the amorphous titanium peroxide sol to decompose the organic substance, i.e. the photocatalytic function, was poorer than that using 100% of the titanium oxide sol. Nevertheless, the amorphous titanium peroxide sol exhibited better adherence, film-forming property, corrosion resistance and decorativeness.

The photocatalytic bodies having a mix of amorphous titanium peroxide sol and titanium oxide sol produced results that were intermediate of those for either of the two sols alone. For example, the color of the colored solution was bleached in 78 hours for a 1:3 mixing ratio of the amorphous titanium peroxide sol and the titanium oxide sol, bleached in 102 hours for a 1:1 mixing ratio, and bleached in 120 hours for a 3:1 mixing ratio, respectively. Accordingly, the photocatalytic function was in reverse proportion to the adherence, film-forming property, corrosion resistance and decorativeness. Thus, a diversity of applications (i.e., substrate material, portions of articles where the photocatalyst is to be applied, and use conditions) may be accommodated by changing the mixing ratio.

Example 2

An acrylic resin plate and a methacrylic acid resin plate were each provided as a substrate. These resin plates were, respectively, immersed in a 2% sodium hydroxide solution at 80° C. for 30 minutes, then washed with water and dried. The amorphous titanium peroxide sol prepared in Reference Solution 1, to which 0.5% of a surface-active agent was added, was coated onto the acrylic resin plate and the methacrylic acid resin plate by repeating a dipping step about 3 or 4 times to form a first layer. Drying was affected at 70° C. for 10 minutes.

A second layer was formed over the first layer by separately coating five different mixtures of the amorphous titanium peroxide sol and the titanium oxide sol at the same mixing ratios used as in Example 1 by repeating a dipping step about 3 or 4 times. Drying and solidification was affected at a temperature of 120° C. for 3 minutes for the acrylic resin plate and was stopped for the methacrylic resin plate when the temperature of a dryer reached 119° C. The results of the photocatalytic function for each plate were similar to those of Example 1. However, the photocatalyst layers that were formed over a first layer had significantly better adhesion to the resin plates and were less likely to decompose the resin plates.

Example 3

A highly water-absorbing and commercially available tile was used as a substrate. The tile was washed with a neutral detergent, dried and applied with a surface-active agent. A photocatalyst formulation was formed by adding 1 part by weight of titanium oxide powder "ST-01" (ISHIHARA SANGYO KAISHA Ltd) to 50 parts of the amorphous titanium peroxide sol (pH 6.4) prepared in Reference 1, followed by mechanical agitation for about 15 minutes and then agitation by means of ultrasonic waves in order not to leave flocs. Dipping was affected at a rate in the range of about 0.3 to about 0.5 cm/second, followed by drying overnight at 30° C. The coated substrate was then baked at 400° C. for 30 minutes to make a photocatalytic layer.

The photocatalyst layer formed in this manner was firmly bonded to the tile surface over a long time. By contrast, merely coating the tile with a dispersion of the titanium oxide powder in distilled water did not result in good bonding.

Example 4

A float glass which had been degreased and treated with a surface-active agent was coated on the surface thereof with a suspension of glass beads by means of a spray gun several times. After drying at 40° C., the coating was baked at 700° C. for 30 minutes. The float glass on which the glass beads were fixed was further coated with a photocatalyst composition used in Example 3, dried and baked at 400° C. for 30 minutes to obtain a photocatalytic layer. This photocatalytic layer was strongly bonded to the glass beads that were fixed on the float glass over a long time.

The terminology used herein is for the purpose of describing particular embodiments only and is not intended to limit the scope of the claims. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, components and/or groups, but do not preclude the presence or addition of one or more other features, integers, steps, operations, elements, components, and/or groups thereof. The terms "preferably," "preferred," "prefer," "optionally," "may," and similar terms are used to indicate that an item, condition or step being referred to is an optional (not required) feature of the embodiment.

The corresponding structures, materials, acts, and equivalents of all means or steps plus function elements in the claims below are intended to include any structure, material, or act for performing the function in combination with other claimed elements as specifically claimed. Embodiments have been presented for purposes of illustration and description, but it is not intended to be exhaustive or limited to the embodiments in the form disclosed. Many modifications and variations will be apparent to those of ordinary skill in the art after reading this disclosure. The disclosed embodiments were chosen and described as non-limiting examples to enable others of ordinary skill in the art to understand these embodiments and other embodiments involving modifications suited to a particular implementation.

What is claimed is:

1. An apparatus, comprising:
   a substrate having a surface; and
   a transparent photocatalyst coating secured on the surface of the substrate, wherein the transparent photocatalyst coating includes titanium oxide, indium tin oxide and silver nitrate.

2. The apparatus of claim 1, wherein the substrate is selected from an appliance handle, doorknob, switch, keyboard, countertop, appliance handle, equipment button, touchscreen, handrail, light emitting device, and light cover.

3. The apparatus of claim 1, wherein the photocatalyst coating is secured to the surface of the substrate by a layer of a binder disposed between the surface of the substrate and the photocatalyst coating, wherein the binder layer is transparent.

4. The apparatus of claim 1, wherein the photocatalyst coating is formed from a mixture including a titanium oxide sol and an amorphous titanium peroxide sol, wherein the mixture includes less than or equal to 30 weight percent (wt %) titanium oxide sol based on a total amount of the titanium oxide sol and the amorphous titanium peroxide sol.

5. The apparatus of claim 4, wherein the photocatalyst coating has been heated to 250 degrees Celsius or greater to convert the amorphous titanium peroxide sol to anatase titanium oxide.

6. The apparatus of claim 1, wherein the photocatalytic coating is formed from a mixture including a titanium oxide sol and an amorphous titanium peroxide sol, wherein the mixture includes between 20 and 80 weight percent (wt %) titanium oxide sol based on a total amount of the titanium oxide sol and the amorphous titanium peroxide sol.

7. The apparatus of claim 6, wherein the photocatalyst coating has been heated to 250 degrees Celsius or greater to convert the amorphous titanium peroxide sol to anatase titanium oxide.

8. The apparatus of claim 1, wherein the transparent photocatalytic coating has a thickness between 2 and 10 micrometers.

9. The apparatus of claim 1, wherein the substrate is an inorganic material selected from ceramic and glass.

10. The apparatus of claim 1, wherein the substrate is an organic material selected from plastic, rubber, wood, and paper.

11. The apparatus of claim 1, wherein the substrate is a metal selected from aluminum, steel and alloys thereof.

12. The apparatus of claim 1, wherein the substrate is an organic polymer resin material selected from acrylonitrile resin, vinyl chloride resin, polycarbonate resins, methyl methacrylate resin, polyester resins, and polyurethane resins.

13. The apparatus of claim 1, wherein the surface of the substrate is a decorative surface, and wherein the appearance of the decorative surface is unimpaired by the presence of the transparent photocatalyst coating on the decorative surface.

14. The apparatus of claim 1, wherein the indium tin oxide reduces a band gap of the transparent photocatalyst coating to 1 electronvolt.

15. The apparatus of claim 1, wherein the transparent photocatalyst coating further includes aluminum zinc oxide.

16. An apparatus, comprising:
a substrate having a surface;
a transparent photocatalyst coating secured on the surface of the substrate, wherein the transparent photocatalyst coating includes titanium oxide and indium tin oxide; and
a transparent binder layer secured between the substrate surface and the transparent photocatalyst coating.

17. The apparatus of claim 16, wherein the surface of the substrate is a decorative surface, and wherein the appearance of the decorative surface is unimpaired by the presence of the transparent photocatalyst coating on the decorative surface.

18. The apparatus of claim 16, wherein the substrate is selected from an appliance handle, doorknob, switch, keyboard, countertop, appliance handle, equipment button, touchscreen, handrail, light emitting device, and light cover.

19. An apparatus, comprising:
a substrate having a surface; and
a transparent photocatalyst coating secured on the surface of the substrate, wherein the transparent photocatalyst coating includes titanium oxide, indium tin oxide, and fluorescent dye.

20. An apparatus, comprising:
a substrate having a surface; and
a transparent photocatalyst coating secured on the surface of the substrate, wherein the transparent photocatalyst coating includes titanium oxide, indium tin oxide, and ultra-fine glitter.

* * * * *